US00PP12384P2

(12) United States Plant Patent
Lamb et al.

(10) Patent No.: US PP12,384 P2
(45) Date of Patent: Feb. 5, 2002

(54) SPATHIPHYLLUM PLANT NAMED 'GRAND DAD'

(75) Inventors: Ann E. Lamb, Sebring; David R. Lilly, Boynton Beach; Randy L. Allamand, Lake Placid, all of FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/588,125

(22) Filed: Jun. 2, 2000

(51) Int. Cl.[7] ..... A01H 5/00
(52) U.S. Cl. ..... Plt./364
(58) Field of Search ..... Plt./364

(56) References Cited

U.S. PATENT DOCUMENTS

PP6,964 P * 8/1989 Georgusis ..... Plt./364

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of Spathiphyllum plant named 'Grand Dad' particularly characterized by its large size and large, wide, dark-green leaves. The leaves of 'Grand Dad' are particularly shiny and relatively flexible, making them less prone to damage from transport. Plants of 'Grand Dad' are large and ideally suited for pot sizes of 20 cm or larger.

4 Drawing Sheets

BACKGROUND OF THE INVENTION

The present invention comprises a new and distinct cultivar of Spathiphyllum plant, botanically known as *Spathiphyllum hybrid*, and hereinafter referred to by the cultivar name 'Grand Dad'.

The new cultivar is the product of a breeding program carried out by the inventors Ann E. Lamb, David R. Lilly and Randy L. Allamand. The new cultivar named 'Grand Dad' is the result of a cross made in Apopka, Fla. in November of 1993. The female parent was a selection of Spathiphyllum 'Mauna Loa' known in the commercial trade as 'Linda' (unpatented). The male parent was a plant, found among seedling-derived Spathiphyllum 'Mauna Loa' named 'Vibrant' (unpatented) which was selected and maintained by the inventors and used only for breeding purposes.

The new cultivar named 'Grand Dad' was discovered and selected by the inventors from a group of seedlings of the stated cross in Homestead, Fla. on Feb. 26, 1996. Propagation by tissue culture in the laboratories of Twyford Plant Laboratories, Inc., in Sebring, Fla., under the supervision of the inventors, was used to increase the number of plants for evaluation and has demonstrated the stability of the combination of characteristics as herein described are firmly fixed and reproduces true to type from generation to generation.

BRIEF DESCRIPTION OF THE INVENTION

The following traits have been repeatedly observed and are determined to be basic characteristics of 'Grand Dad' which in combination distinguish this Spathiphyllum as a new and distinct cultivar:

1. Plants are large and ideally suited for pot sizes of 20 cm or larger;

2. Leaves are dark-green, large and broad with a shiny surface;

3. Spathes are large, ovate, cupped and are held just above the foliage on thick, sturdy peduncles. The spathes are pale green in color when newly open, becoming green with age; and 4. Foliage is well adapted to commercial shipping practices because it is flexible and does not damage easily.

'Grand Dad' has not been observed under all possible environmental conditions. The phenotype of the new cultivar may vary significantly with variations in environment such as temperature, light intensity, and daylength, without any change in genotype.

Of the commercial cultivars known to the inventors, the most similar in comparison to 'Grand Dad' is the cultivar 'Gorgusis No. 1' (U.S. Plant Pat. No. 6,964 and known in the commercial trade as 'Sensation R'). In comparison to 'Gorgusis No. 1', the leaves of 'Grand Dad' have a shinier surface than the leaves of 'Gorgusis No. 1'. The growth habit of 'Gorgusis No. 1' is more upright than that of 'Grand Dad'. The foliage of 'Grand Dad' is flexible while the foliage of 'Gorgusis No. 1' is often brittle.

The female parent 'Linda' is a large, upright growing variety used in 10–14 inch pots, with broad dark green leaves and large, bright white spathes held above the foliage. In comparison to 'Linda', 'Grand Dad' is a larger plant and has larger, broader leaves with very glossy and shiny surfaces.

The male parent 'Vibrant' is a very large plant with very large, shiny leaves and green spathes which are held just above the foliage. In comparison to 'Vibrant', the growth habit of Spathiphyllum 'Grand Dad' is more upright and compact, and plants of 'Grand Dad' are more likely to branch than those of 'Vibrant'. The spathes of 'Grand Dad' are pale green when newly open. The spathes of 'Vibrant' are darker green when newly open, and are larger than those of 'Grand Dad'.

BRIEF DESCRIPTION OF THE DRAWING

The accompanying color photographic illustrations show typical characteristics of a 12-month-old plant of 'Grand Dad' grown in a 20-cm pot initiated from three microcuttings obtained by tissue culture and grown under appropriate growing conditions, with colors being as nearly true as possible with illustrations of this type.

Sheet 1 is a side view showing the inflorescence and foliage of a plant of 'Grand Dad'.

Sheet 2 is a close-up view of the inflorescence of the instant plant.

Sheet 3 illustrates the upper leaf surface.

Sheet 4 illustrates the lower leaf surface.

DETAILED BOTANICAL DESCRIPTION

The following observations, measurements and values describe 15 month old plants, finished in 25 cm pots, as grown in Homestead, Fla. under greenhouse conditions which closely approximate those generally used in horticultural practice. All color references are measured against The Royal Horticultural Society (R.H.S.) Colour Chart. Colors are approximate as color depends on horticultural practices such as light level and fertilization rate, among others, without, however, any variance in genotype.

Classifiction:

*Commercial.*—*Spathiphyllum hybrid* cv. 'Grand Dad'.

Parentage:

*Male parent.*—Selection of Spathiphyllum 'Mauna Loa' named 'Vibrant'.

*Female parent.*—Selection of Spathiphyllum 'Mauna Loa' named 'Linda'.

Propagation: Vegetative, by tissue culture.

Plant: Under appropriate growing conditions, plant attains a size of approximately 72 cm to 80 cm in height from the soil plane to the tip of the spathe, and approximately 100 cm to 120 cm in width.

Leaves:

*Form.*—The leaf blade is ovate with an obtuse base and an acuminate to cuspidate apex which curves downward. The margins are entire and slightly wavy. The midrib is straight over approximately ⅔ the length of the leaf, and curved downward somewhat toward the leaf tip. The leaves are leathery and flexible. The upper leaf surface is textured and shiny.

*Size.*—Leaf blades are approximately 36 cm to 42 cm in length and approximately 18.5 cm to 26 cm width.

*Petiole.*—Approximately 38 cm to 45 cm in length from the base of the petiole to the base of the leaf blade on primary shoots. The petiole is approximately 9 mm in diameter at the junction of the geniculum and petiole sheath. The portion of the petiole below the geniculum is straight.

*Petiole sheath.*—Approximately 30 cm to 40 cm in length and approximately 10 mm to 14 mm in width at the midpoint. The tip of the petiole sheath is bluntly rounded or tapered flush with the petiole. The petiole sheath terminates at or about 1.8 cm below the base of the geniculum.

*Geniculum.*—Approximately 6.2 cm to 9.1 cm in length and approximately 1.15 cm in diameter. The color is darker than, but closest to, RHS 146B.

*Veins.*—Veins are sunken and the leaf blade convex between veins on the upper surface giving the leaf a textured appearance. The midrib is sunken. Well defined primary veins radiate out from the midrib over the length of the leaf. There are approximately 15 pairs of primary veins on the leaf.

*Color.*—Leaf: Upper surface: Greener than, but closest to, RHS 139A. Lower surface: Darker than, but closest to, RHS 137B to RHS 137C. Midrib: Upper surface: Darker than, but closest to, RHS 137A to RHS 137B. Lower surface: RHS 146C. Petiole: Darker and greener than, but closest to, RHS 137A. Petiole sheath: Darker and greener than, but closest to, RHS 137A.

Inflorescence:

*Immature.*—The spathe is tightly rolled around the spadix and emerges from the petiole sheath. The spathe is fully open approximately when the peduncle is fully elongated — approximately 85 cm to 90 cm above the soil surface, measured at the tallest point. The peduncle is approximately 68 cm to 74 cm in length measured from the crown of the plant to the base of the spathe. The peduncle is approximately 8 mm to 9 mm in diameter measured at the midpoint of the peduncle. The peduncle is darker and greener than, but closest to, RHS 146A to RHS 146B.

*Mature.*—Spathe Size: The spathe is approximately 19.0 cm to 24.5 cm long and approximately 11.0 cm to 13.5 cm in width. It is cupped, approximately 3.0 cm in depth. Color: Unopened bud: Yellow-green, RHS 145C to RHS 145D. Fully open: Front surface: Yellow-green, RHS 145D, tinged with RHS 150D along the midrib. Back surface: Yellow-green, RHS 145C to RHS 145D with areas of RHS 145A. Midrib of back surface is greener than, but closest to, RHS 146B. Apex: Front is RHS 145 D tinged with 150 D; the back is RHS 146C. Faded: Front surface: RHS 145A to RHS 145B streaked with RHS 146B. Back surface: Darker and greener than, but closest to, RHS 145A streaked with RHS 146B; midrib is greener than, but closest to, RHS 146B. Apex: The front is RHS 145 A, the back is RHS 146B to RHS 146C.

*Arrangement.*—The spathe terminates as a thick, straight peduncle which opens vertically just above the leaves.

*Shape.*—The spathe is broadly ovate with an obtuse base and an acuminate, twisted apex.

*Margins.*—Smooth with occasional undulations, entire.

*Flowering.*—Depending on season, approximately 2 to 3 inflorescences typically present on plants. Smaller inflorescences may occur on less mature growth.

*Fragrance.*—Sweet, pleasant, moderately fragrant, most noticeable in the morning.

*Lastingness of the individual inflorescence.*—Spathes of 'Grand Dad' begin to change from pale green to darker green after about 2 weeks, becoming almost entirely green after about 4 weeks. Cut inflorescences last about 7 days off the plant.

Reproductive organs:

*Spadix.*—Size: Approximately 10 cm in length and approximately 1.7 cm in diameter. Quantity: Approximately 250 flowers per spadix. Color: When the spathe unrolls, the spadix is RHS 158B to RHS 158C gradually changing to green, RHS 146C, as the inflorescence ages. Stamens: Firmly affixed against the pistil. Not clearly visible until pollen is produced. Pollen: RHS 158D. Pistil: RHS 158B to RHS 158C in color, conical, protruding between the staminate flowers, fixed to the main axil. One pistil per flower. The pistillate flowers extend approximately 3.0 mm beyond the staminate flowers.

Seeds: Approximately 2 mm in diameter, reniform in shape, light to medium brown in color. Surface texture of seed coat is pitted. Each individual capsule contains approximately 1–6 seeds. Depending on size and degree of pollination, a single inflorescence can yield 750+ seeds.

Fruit: Oblong to elliptic berry, 7 mm long and 5 mm wide, yellow RHS 19B tinged with RHS 146C when ripe.

Roots: Thick, white roots with abundant fine laterals.

Pest/disease/resistance susceptibility: Preventative disease and pest control measures used to grow crops of 'Grand Dad' are typical of ordinary commercial practice. 'Grand Dad' has no sensitivity to common pests or pathogens observed to date.

We claim:

1. A new and distinct cultivar of Spathiphyllum plant named 'Grand Dad', as illustrated and described.

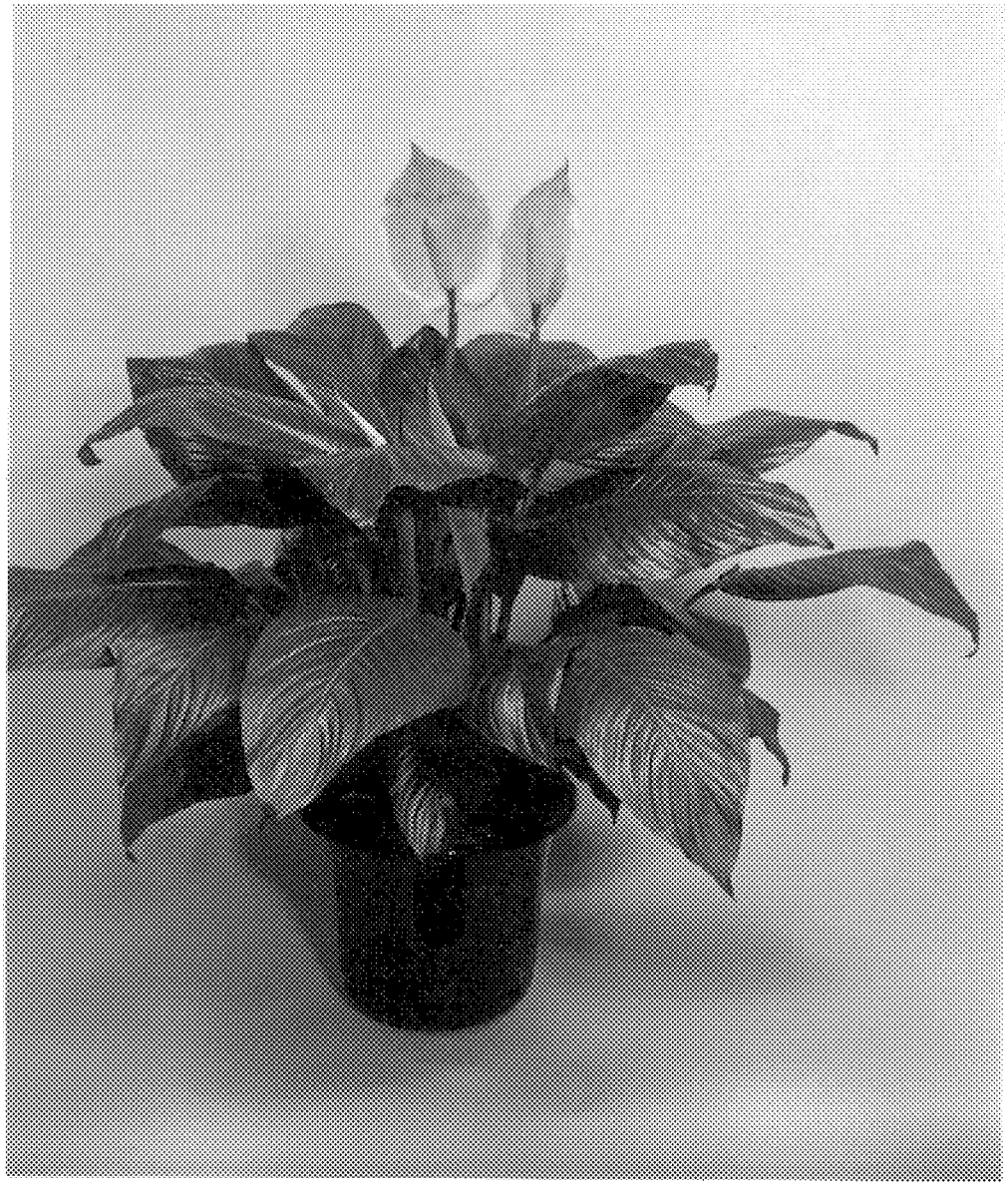

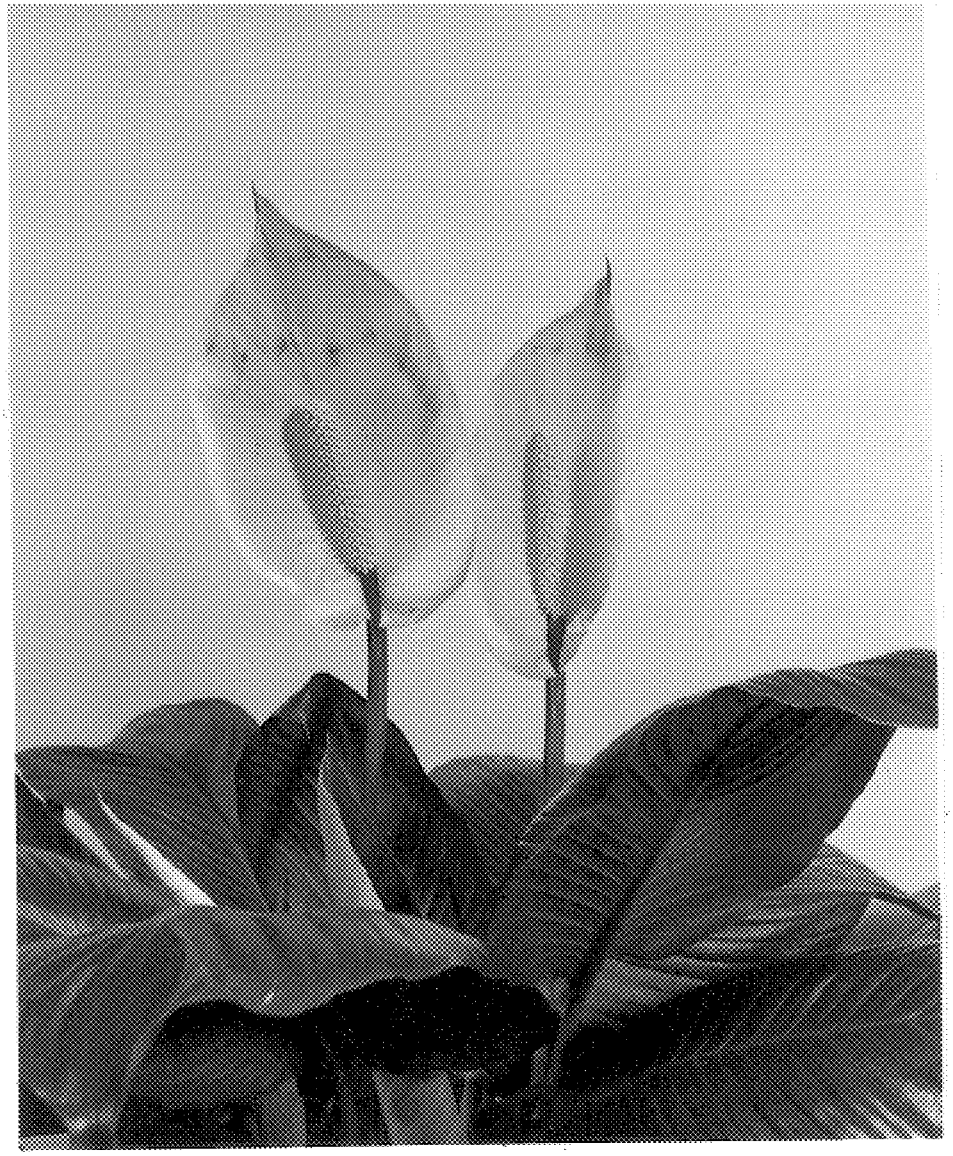

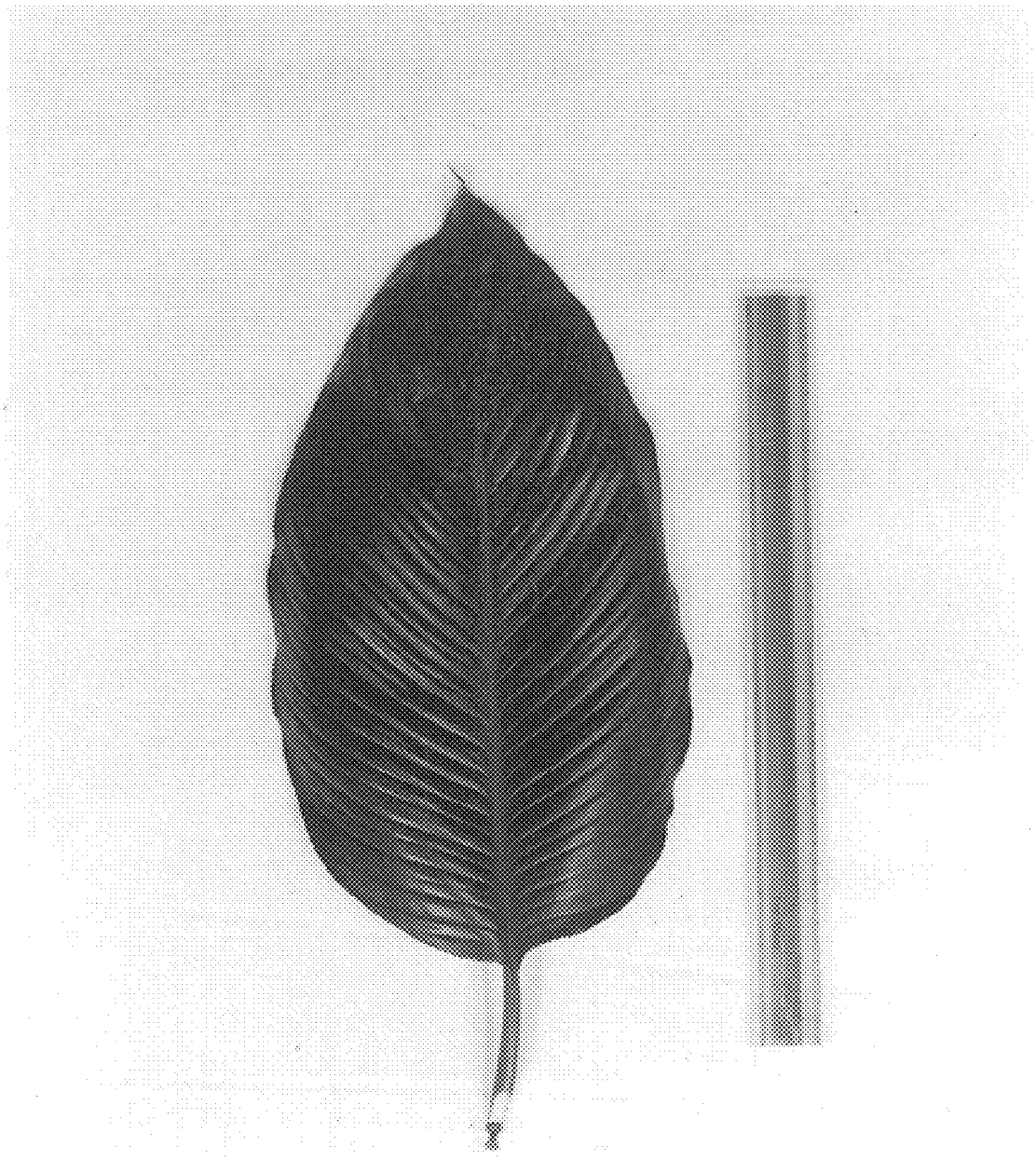

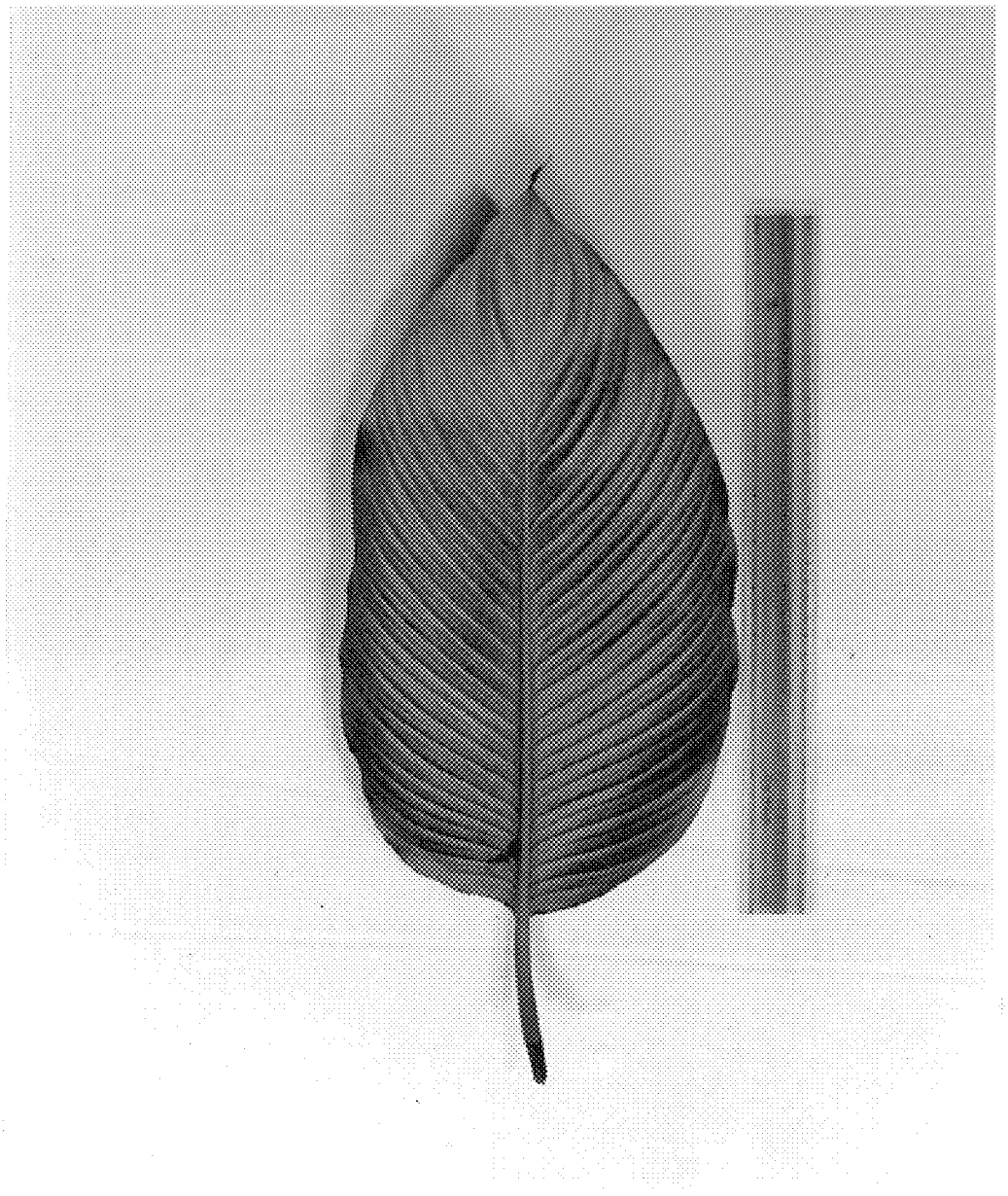

* * * * *